(12) United States Patent
Sullivan et al.

(10) Patent No.: US 7,850,663 B2
(45) Date of Patent: *Dec. 14, 2010

(54) MEDICAMENT MICRODEVICE DELIVERY SYSTEM, CARTRIDGE AND METHOD OF USE

(75) Inventors: Vincent J. Sullivan, Cary, NC (US); Ronald J. Pettis, Cary, NC (US); John A. Mikszta, Durham, NC (US); John P. Dekker, III, Cary, NC (US); Wendy D. Woodley, Cary, NC (US); Anjana Bhuta Wills, Cary, NC (US); Matthew S. Ferriter, Chapel Hills, NC (US); C. Robin Hwang, Thousand Oaks, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1812 days.

This patent is subject to a terminal disclaimer.

(21) Appl. No.: 10/858,447

(22) Filed: Jun. 1, 2004

(65) Prior Publication Data

US 2005/0000514 A1 Jan. 6, 2005

Related U.S. Application Data

(63) Continuation-in-part of application No. 10/141,849, filed on May 10, 2002, now Pat. No. 6,782,887, which is a continuation-in-part of application No. 09/879,517, filed on Jun. 12, 2001, now Pat. No. 6,929,005, which is a continuation-in-part of application No. 09/758,776, filed on Jan. 12, 2001, now Pat. No. 6,722,364.

(60) Provisional application No. 60/474,592, filed on Jun. 2, 2003.

(51) Int. Cl.
*A61M 5/00* (2006.01)
(52) U.S. Cl. ......................................... 604/232; 604/87
(58) Field of Classification Search ............. 604/82–92, 604/139, 140, 148, 149, 200–206, 232, 47, 604/244, 415
See application file for complete search history.

(56) References Cited

U.S. PATENT DOCUMENTS 3,494,359 A 2/1970 Zackheim
(Continued)

FOREIGN PATENT DOCUMENTS

| EP | 1086718 A | 3/2001 |
|----|-----------|--------|
| JP | 32-8743 | 10/1952 |
| JP | 48-91797 | 3/2001 |
| WO | WO 02/05889 A | 1/2002 |
| WO | WO0205889 A | 1/2002 |

OTHER PUBLICATIONS

WO 02/056950 A3 PCT Search Report.

*Primary Examiner*—Kevin C Sirmons
*Assistant Examiner*—Catherine N Witczak
(74) *Attorney, Agent, or Firm*—Robert E. West

(57) ABSTRACT

A method and device for intradermal delivery of a reconstituted powdered medicament. The device includes a chamber, which is in fluid communication with a microdevice, e.g. microabrader or one or more microneedles. A cartridge containing the powdered medicament may be located within said chamber. At least one burstable membrane retains a powdered medicament within the housing. The method involves the steps of positioning the device at a delivery site on the skin of a patient and intradermally administering the medicament by dispensing a diluent from a diluent source an through inlet port to rupture the membranes, reconstitute the powdered medicament and deliver the reconstituted medicament through the microdevice to the dermal region of the skin.

23 Claims, 16 Drawing Sheets

U.S. PATENT DOCUMENTS

Figure 1:
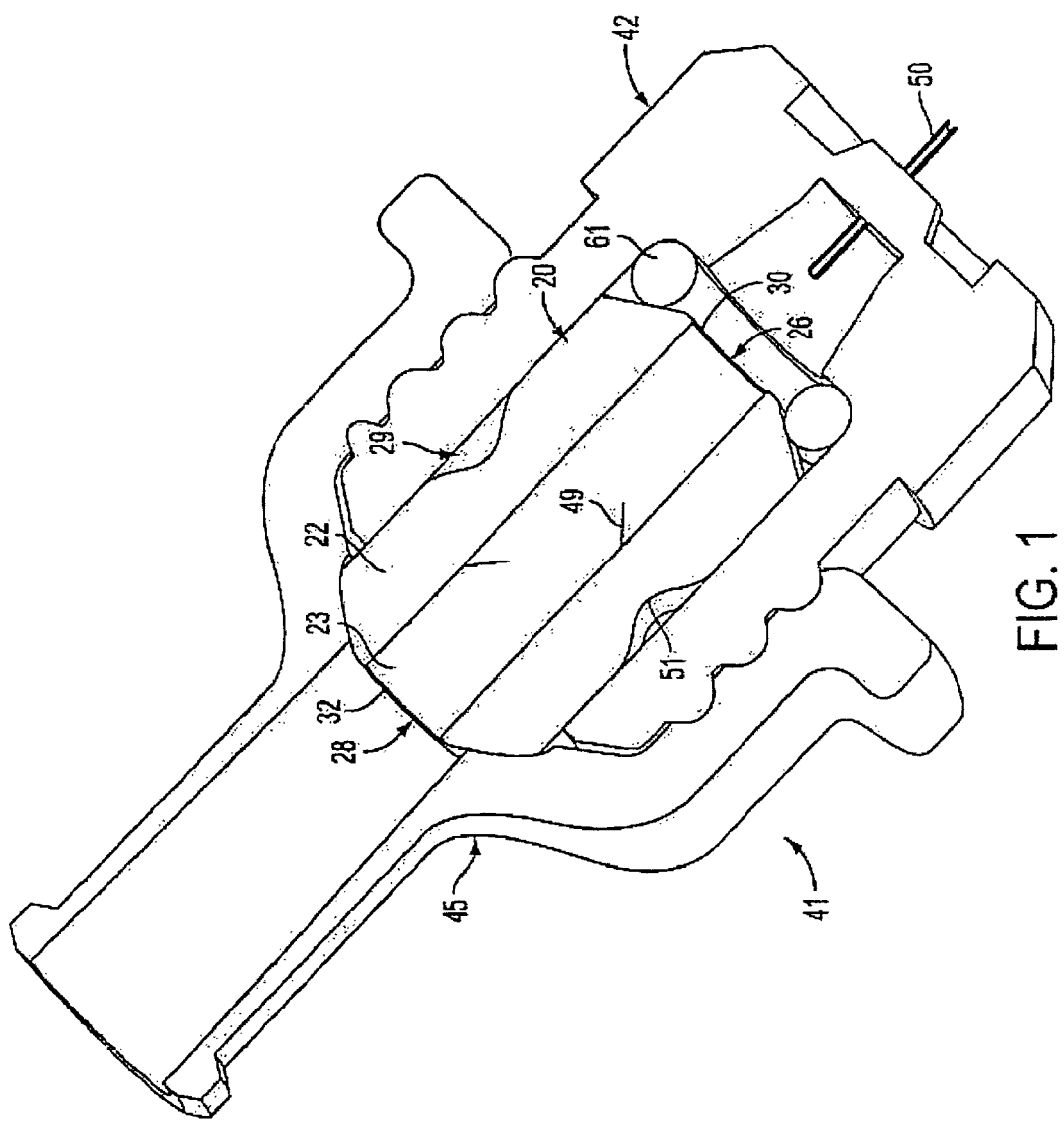
Figure 2:
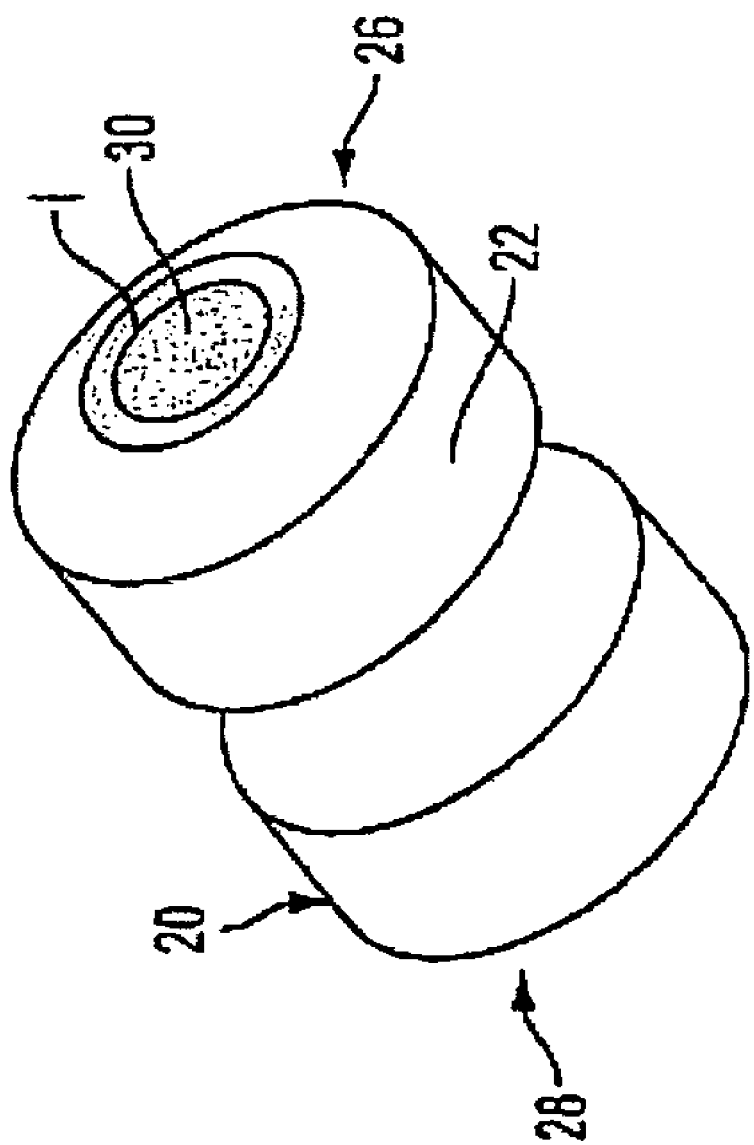
Figure 3:
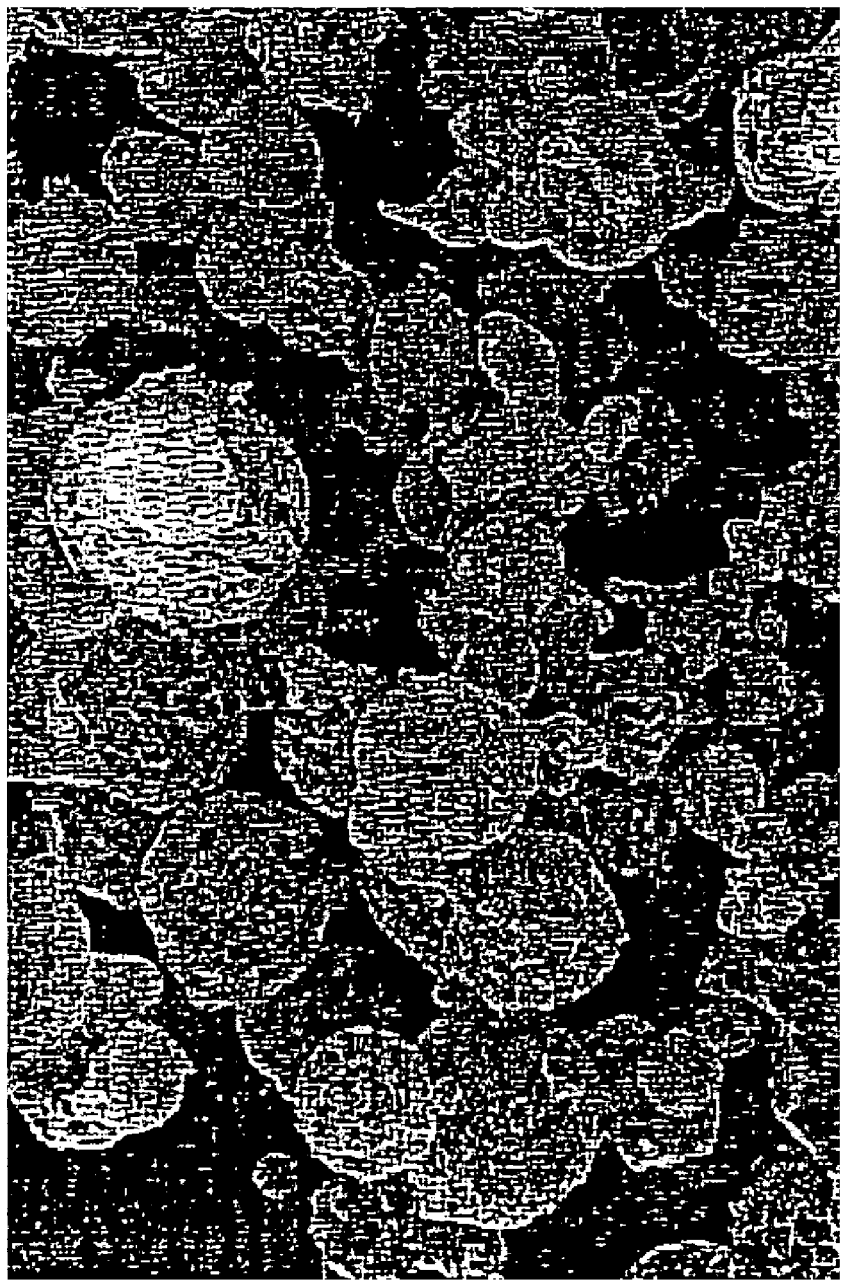

| | | | |
|---|---|---|---|
| 3,595,439 A | 7/1971 | Newby et al. | |
| 3,625,213 A | 12/1971 | Brown | |
| 3,756,390 A | 9/1973 | Abdey et al. | |
| 4,412,836 A | 11/1983 | Brignola | |
| 4,599,082 A | 7/1986 | Grimard | |
| 5,354,278 A * | 10/1994 | Kriesel | 604/132 |
| 5,411,175 A | 5/1995 | Armstrong et al. | |
| 5,531,683 A * | 7/1996 | Kriesel et al. | 604/89 |
| 5,637,087 A | 6/1997 | O'Neil et al. | |
| RE35,986 E | 12/1998 | Ritson et al. | |
| 6,024,721 A | 2/2000 | Wong et al. | |
| 6,387,074 B1 | 5/2002 | Horppu et al. | |
| 6,443,152 B1 | 9/2002 | Lockhart et al. | |
| 6,558,358 B2 | 5/2003 | Rosoff et al. | |
| 6,562,002 B1 | 5/2003 | Taylor | |
| 6,641,561 B1 | 11/2003 | Hill et al. | |
| 6,641,565 B1 | 11/2003 | Lavi et al. | |
| 6,656,150 B2 | 12/2003 | Hill et al. | |
| 6,702,778 B2 | 3/2004 | Hill et al. | |
| 6,723,068 B2 | 4/2004 | Lavi et al. | |
| 7,011,650 B2 | 3/2006 | Rosoff et al. | |
| 2002/0082543 A1* | 6/2002 | Park et al. | 604/21 |
| 2002/0092524 A1 | 7/2002 | Lockhart et al. | |
| 2002/0169416 A1 | 11/2002 | Gonnelli et al. | |
| 2003/0028142 A1 | 2/2003 | Nobbio | |
| 2003/0187388 A1 | 10/2003 | Sharon et al. | |

* cited by examiner

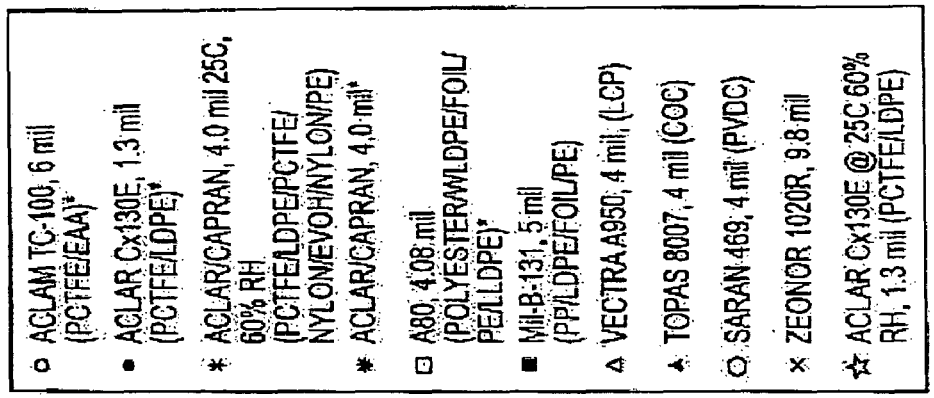
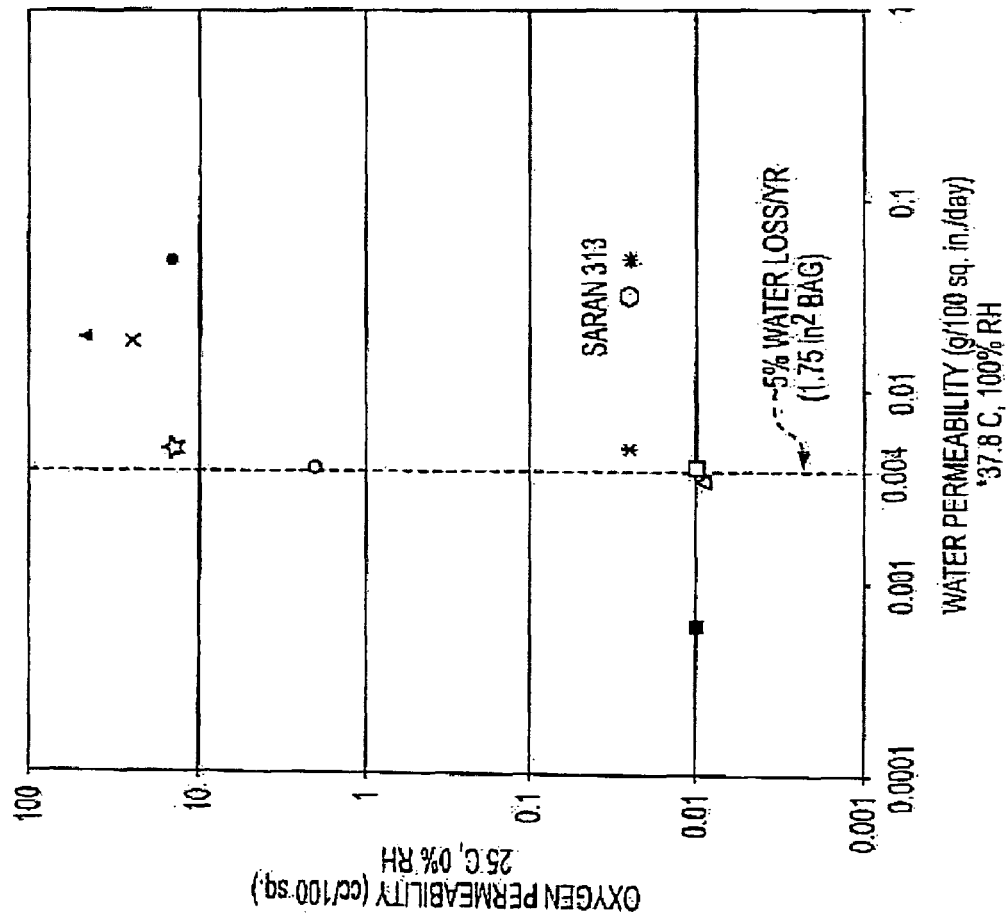
FIG. 10

MEDICAMENT MICRODEVICE DELIVERY SYSTEM, CARTRIDGE AND METHOD OF USE

CROSS REFERENCE TO RELATED APPLICATIONS

This application claims priority to U.S. Provisional application 60/474,592 filed Jun. 2, 2003 and is a continuation-in-part of U.S. patent application Ser. No. 10/141,849 Filed May 10, 2002, now U.S. Pat. No. 6,782,887 which is a continuation in part of Ser. No. 09/879,517 filed Jun. 12, 2001 now U.S. Pat. No. 6,929,005 issued Sep. 3, 2002, which is a continuation in part of Ser. No. 09/758,776 filed Jan. 12, 2001 now U.S. Pat. No. 6,722,364, issued Apr. 1, 2004 all of which are herein incorporated by reference, in their entirety.

FIELD OF THE INVENTION

This invention relates to intradermal medicament delivery devices including microabraders or microneedles, and their use to deliver a powdered medicament to a subject.

BACKGROUND OF THE INVENTION

The importance of efficiently and safely administering pharmaceutical substances such as diagnostic agents and drugs has long been recognized. Although an important consideration for all pharmaceutical substances, obtaining adequate bioavailability of large molecules such as proteins that have arisen out of the biotechnology industry has recently highlighted this need to obtain efficient and reproducible absorption (Cleland et al., *Curr. Opin. Biotechnol.* 12: 212-219, 2001). The use of conventional needles has long provided one approach for delivering pharmaceutical substances to humans and animals by administration through the skin. Considerable effort has been made to achieve reproducible and efficacious delivery through the skin while improving the ease of injection and reducing patient apprehension and/or pain associated with conventional needles. Furthermore, certain delivery systems eliminate needles entirely, and rely upon chemical mediators or external driving forces such as iontophoretic currents or electroporation or thermalporation or sonophoresis to breach the stratum corneum, the outermost layer of the skin, and deliver substances through the surface of the skin. However, such delivery systems do not reproducibly breach the skin barriers or deliver the pharmaceutical substance to a given depth below the surface of the skin and consequently, clinical results can be variable. Thus, mechanical breach of the stratum corneum, such as with needles, is believed to provide the most reproducible method of administration of substances through the surface of the skin, and to provide control and reliability in placement of administered substances.

Approaches for delivering substances beneath the surface of the skin have almost exclusively involved transdermal administration, i.e. delivery of substances through the skin to a site beneath the skin. Transdermal delivery includes subcutaneous, intramuscular or intravenous routes of administration of which, intramuscular (IM) and subcutaneous (SC) injections have been the most commonly used.

Anatomically, the outer surface of the body is made up of two major tissue layers, an outer epidermis and an underlying dermis, which together constitute the skin (for review, see *Physiology, Biochemistry, and Molecular Biology of the Skin, Second Edition*, L. A. Goldsmith, Ed., Oxford University Press, New York, 1991). The epidermis is subdivided into five layers or strata of a total thickness of between 75 and 150 µm. Beneath the epidermis lies the dermis, which contains two layers, an outermost portion referred to at the papillary dermis and a deeper layer referred to as the reticular dermis. The papillary dermis contains vast microcirculatory blood and lymphatic plexuses. In contrast, the reticular dermis is relatively acellular and avascular and made up of dense collagenous and elastic connective tissue. Beneath the epidermis and dermis is the subcutaneous tissue, also referred to as the hypodermis, which is composed of connective tissue and fatty tissue. Muscle tissue lies beneath the subcutaneous tissue.

As noted above, both the subcutaneous tissue and muscle tissue have been commonly used as sites for administration of pharmaceutical substances. The dermis, however, has rarely been targeted as a site for administration of substances, and this may be due, at least in part, to the difficulty of precise needle placement into the intradermal space. Furthermore, even though the dermis, in particular, the papillary dermis has been known to have a high degree of vascularity, it has not heretofore been appreciated that one could take advantage of this high degree of vascularity to obtain an improved absorption profile for administered substances compared to subcutaneous administration. This is because small drug molecules are typically rapidly absorbed after administration into the subcutaneous tissue, which has been far more easily and predictably targeted than the dermis has been. On the other hand, large molecules such as proteins are typically not well absorbed through the capillary epithelium regardless of the degree of vascularity so that one would not have expected to achieve a significant absorption advantage over subcutaneous administration by the more difficult to achieve intradermal administration even for large molecules.

One approach to administration beneath the surface to the skin and into the region of the intradermal space has been routinely used in the Mantoux tuberculin test. In this procedure, a purified protein derivative is injected at a shallow angle to the skin surface using a 27 or 30 gauge needle (Flynn et al, *Chest* 106: 1463-5, 1994). A degree of uncertainty in placement of the injection can, however, result in some false negative test results. Moreover, the test has involved a localized injection to elicit a response at the site of injection and the Mantoux approach has not led to the use of intradermal injection for systemic administration of substances.

As taught by published US application US 2003/0050602, when a microneedle system is used for in vivo delivery, such as delivery to an intradermal space, a significant backpressure is encountered due to instillation rate of fluid volume into and essentially sealed or closed space having limited distensibility. This is true even though intradermal delivery of substances, such as medications, involve much smaller volumes if liquid, 100:L (microliters) for example, as compared with the volumes used in subcutaneous systems, which can be as large or larger than 500:L (microliters). The magnitude of backpressure is also proportional to both the instillation rate as well as the volume. This level of pressure is not typically encountered when delivering a substance to the subcutaneous or intramuscular space, which is generally regarded as a region of highly distensable tissue with a much higher limit for instilled volume.

Some groups have reported on systemic administration by what has been characterized as "intradermal" injection. In one such report, a comparison study of subcutaneous and what was described as "intradermal" injection was performed (Autret et al, *Therapie* 46:5-8, 1991). The pharmaceutical substance tested was calcitonin, a protein of a molecular weight of about 3600. Although it was stated that the drug was injected intradermally, the injections used a 4 mm needle pushed up to the base at an angle of 60. This would have resulted in placement of the injectate at a depth of about 3.5 mm and into the lower portion of the reticular dermis or into the subcutaneous tissue rather than into the vascularized papillary dermis. If, in fact, this group injected into the lower portion of the reticular dermis rather than into the subcutaneous tissue, it would be expected that the substance would either be slowly absorbed in the relatively less vascular reticular dermis or diffuse into the subcutaneous region to result in what would be functionally the same as subcutaneous administration and absorption. Such actual or functional subcutaneous administration would explain the reported lack of difference between subcutaneous and what was characterized as intradermal administration, in the times at which maximum plasma concentration was reached, the concentrations at each assay time and the areas under the curves.

Similarly, Bressolle et al. administered sodium ceftazidime in what was characterized as "intradermal" injection using a 4 mm needle (Bressolle et al., J. Pharm. Sci. 82:1175-1178, 1993). This would have resulted in injection to a depth of 4 mm below the skin surface to produce actual or functional subcutaneous injection, although good subcutaneous absorption would have been anticipated in this instance because sodium ceftazidime is hydrophilic and of relatively low molecular weight.

Another group reported on what was described as an intradermal drug delivery device (U.S. Pat. No. 5,997,501). Injection was indicated to be at a slow rate and the injection site was intended to be in some region below the epidermis, i.e., the interface between the epidermis and the dermis or the interior of the dermis or subcutaneous tissue. This reference, however, provided no teachings that would suggest a selective administration into the dermis nor did the reference suggest any possible pharmacokinetic advantage that might result from such selective administration.

Other methods of increasing skin permeability use various chemical permeation enhancers or electrical energy such as electroporation. Ultrasonic energy such as sonophoresis and laser treatments has been used. These methods require complex and energy intensive electronic devices that are relatively expensive. The chemical enhancers are often not suitable for intradermal drug delivery or sampling.

One example of a method for increasing the delivery of drugs through the skin is iontophoresis. Iontophoresis generally applies an external electrical field across the skin. Ionic molecules in this field are moved across the skin due to the force of the electric field. The amount and rate of drug delivery using iontophoresis can be difficult to control. Iontophoresis can also cause skin damage on prolonged exposure.

Sonic, and particularly ultrasonic energy, has also been used to increase the diffusion of drugs through the skin. The sonic energy is typically generated by passing an electrical current through a piezoelectric crystal or other suitable electromechanical device. Although numerous efforts to enhance drug delivery using sonic energy have been proposed, the results generally show a low rate of drug delivery.

Other forms of transdermal drug delivery are also known, and one such form uses pulsed laser light to ablate the stratum corneum without significant ablation or damage to the underlying epidermis. A drug is then applied to the ablated area and allowed to diffuse through the epidermis.

Another method of delivering drugs through the skin is by forming micro pores or cuts through the stratum corneum. Piercing the stratum corneum and delivering the drug to the tissue below the stratum corneum can effectively administer many drugs. The devices for piercing the stratum corneum generally include a plurality of micron-size needles or blades having a length to pierce the stratum corneum without passing completely through the epidermis. Examples of these devices are disclosed in U.S. Pat. Nos. 5,879,326 and 6,454,755 to Godshall et al.; U.S. Pat. No. 5,250,023 to Lee et al.; WO 97/48440; and WO 00/74763.

The prior methods and apparatus for the transdermal administration of drugs have exhibited limited success. Accordingly, a continuing need exists in the industry for an improved device for the intradermal administration of various drugs and other substances.

Presently, storage-stability can be imparted to medicaments by placing them in a dry powder form. Techniques for doing this include freeze-drying, spray freeze-drying, lyophilization and the like. Some dry powdered medicaments have been directly administered by inhalation. See WO 95/24183 which relates to a dry powder form of insulin for inhalation.

To date, however, there remains a need for a system for the intradermal administration of medicaments where the medicament is in a storage stable dry form, which can be readily reconstituted and directly administered via microdelivery devices such as, microabraders or microneedles and wherein the system utilizes the inherent backpressure of such intradermal or epidermal delivery to assist in the fluidic reconstitution of the dry medicament.

SUMMARY OF THE INVENTION

The present invention involves devices and methods that integrate the essentially simultaneous fluidic reconstitution of a powdered medicament with the intradermal delivery or epidermal delivery of that fluid via a micro-delivery device (microdevice). Microdevices for disrupting the stratum corneum include microabraders and micron-sized needles (microneedles) or blades having a length to penetrate and substantially pierce the stratum corneum without substantially penetrating into the underlying dermis. Microneedles include structures with a diameter equivalent to or smaller than about 30 gauge, typically about 30-40 gauge when such structures are cylindrical in nature. Non-cylindrical structures encompassed by the term microneedles would therefore be of comparable diameter and include pyramidal, rectangular, octagonal, wedge, and other suitable geometrical shapes.

The devices of this invention exploit the benefits of having a dry powdered medicament formulation in conjunction with the increased bioavailability and efficient delivery of microdevices. Medicaments can include pharmaceuticals, such as biopharmaceuticals, vaccines and nutrients including nutraceuticals, as well as such substances as anti-venom and antidotes for those exposed to poisons or biological agents, for example. An example of such dry powders which may be used in the instant invention are described in U.S. patent application Ser. Nos. 10/299,012 and 10/299,010 which are herein incorporated by reference in its entirety.

In some embodiments the dry powdered medicament can be stored and retained within a cavity in a housing. In one aspect of the invention a medicament is stored in a pre-filled carrier ("cartridge") and is retained within the cartridge by two rupturable or pierceable films or membranes sealed to either end of the cartridge. The cartridge, when present, is placed into a cavity contained within the housing. The housing may also comprise an adapter, which is in fluid communication with the housing cavity and may be in the form of, for example, a tube or conduit. The adapter may also contain a connector such as a Luer fitting that marries to a standard syringe or some other source of liquid fluid such as a blow-fill seal container, liquid filled bulb or bladder, for example. The medicament delivery end of the device comprises a microdevice, e.g. a microabrader, or one or more microneedles, which is in fluid communication with the cavity of the housing containing the medicament. A source of a solvent ("diluent") may be attached to the housing via the adapter in a removable fashion or may be permanently attached, or integral with the housing. Regardless, the fluid diluent is not in contact with the dry powder prior to actuation of the device. To actuate the device, the user depresses on the plunger of the syringe or squeezes the bulb or otherwise activates the flow of diluent, discharging the fluid and rupturing the membranes retaining the powdered medicament through the use of pressure or mechanical piercing elements, exposing the dry powder to the diluent. With the presence of backpressure normally encountered with intradermal delivery, the residence contact time of the diluent and the powered medicament is improved and assists with the reconstitution process. The same is true for epidermal delivery, since the skin contacting an epidermal type device may act as a flow restrictor. The increased pressure generated by the user's depression of the syringe or other activating mechanism essentially simultaneously forces the diluent into the chamber containing the powdered medicament, the reconstitution of that powdered medicament and the ejection of the formed diluent/medicament solution out of the housing and into the skin intradermally via the microdevice. In another aspect of the invention, the membrane is ruptured with the aid of a piercing element simultaneously with activation of the device. In another embodiment, the membrane is ruptured by a piercing element just prior to activation of the device.

In one aspect, the invention provides a method for the intradermal delivery of a substance to a subject by positioning the device of this invention at a delivery site on the skin of a patient, intradermally administering the medicament by applying the microdevice of the instant intradermal delivery device to the intradermal region of the skin of the subject, dispensing a diluent into the intradermal delivery device through the inlet port with sufficient force to rupture the at least one burstable membrane, reconstituting the powdered medicament with the dispense diluent and substantially simultaneously delivering the reconstituted medicament through the outlet port to the microdevice at a delivery rate slower than the delivery rate of the diluent to the delivery device.

In another aspect, the invention provides a method for the intradermal delivery of a substance to a subject by positioning the device of this invention at a delivery site on the skin of a patient, intradermally administering the medicament by applying the microdevice of the instant intradermal delivery device to the intradermal region of the skin of the subject, dispensing a diluent into the intradermal delivery device through the inlet port while simultaneously piercing a membrane, reconstituting the powdered medicament with the dispense diluent and substantially simultaneously delivering the reconstituted medicament through the outlet port to the microdevice at a delivery rate slower than the delivery rate of the diluent to the delivery device. In another aspect of the invention, the membrane is pierced just prior to activation of the device.

BRIEF DESCRIPTION OF THE DRAWINGS

FIG. 1 shows in cross section, a device that incorporate a microneedle.

FIG. 2 shows a pre-filled carrier of one aspect the invention with heat-sealed rupture membranes.

FIG. 3 shows a micrograph of the particles of SFD powders of one aspect the invention.

FIG. 4 depicts a schematic side view of a device showing one aspect the invention utilizing microabraders as the delivery means.

FIGS. 5A, B, C, and D show one aspect the invention which incorporates piercing elements to mechanically rupture the membranes in various stages of its operation.

FIG. 6 is an exploded view of the embodiment of a microneedle delivery device shown in FIG. 1.

FIG. 7 is a graph depicting the results of using the microneedle embodiment of FIG. 6 to administer reconstituted 'pure SFD insulin, i.e. without addition of cryoprotectant excipients.

FIG. 8 is a graph depicting the results of using the microneedle embodiment of FIG. 6 to administer an insulin/trehalose formulation.

FIG. 9 is a bar graph depicting the emitted dose results in terms of percent-emitted dose versus diluent volumes utilizing the device of FIG. 6.

FIG. 10 shows water and oxygen barrier properties for a range of commercially available barrier films.

FIG. 11 shows the results of the testing described in ample 3.

FIG. 12 shows a schematic of a pump device, which incorporates aspects of the invention.

FIG. 13 shows a cross-sectional schematic view of a device, which shows a sliding piercing element of one aspect of the invention.

DETAILED DESCRIPTION OF THE INVENTION

In one aspect the invention, the intradermal medicament delivery devices comprises a housing comprising a chamber, an inlet port communicating with the chamber and an outlet port communicating with the chamber and a microdevice portion of the device. Optionally, the outlet port is coaxially aligned with the inlet port. The microdevice comprises one or more microneedle or microabrader surfaces. A dry powdered medicament is located within the housing chamber and preferably contained within a cartridge comprising at least one fluid receiving opening and at least one fluid discharge opening. The cartridge also comprises at least one passage or cavity within. When placed within the housing chamber, the at least one receiving and the at least one discharge openings of the cartridge are aligned with the inlet and outlet ports of the housing. The medicament is placed in the cartridge cavity or housing chamber and preferably at least one burstable, polymeric membrane covers the passage at each of the fluid receiving and discharge ends of the housing or cartridge. Such polymeric membranes may be burstable either by pressure or by the use of one or more piercing element(s). The terms 'burstable' or 'rupturable' are used interchangeably herein and are meant to indicate disruption of the barrier properties of the barrier material by some means inter alia piercing or mechanical fracture. In one embodiment, the housing can be formed of two releasably interconnected parts providing access to the chamber for replacement of a disposable, prefilled medicament cartridge. The releasable connection can be attained in a variety of ways including threaded attachment, a snap fit arrangement, clamps, bayonets, or other means known to those in the art. Snap fit attachment is most preferred for ease of assembly. The intradermal delivery device may also include an adapter communicating with the chamber for receipt or attachment of a fluid delivery device, such as a syringe barrel or compressible bulb or bladder. If a syringe is to be used the adapter preferably includes a Luer connector adapted to receive a syringe barrel for supplying fluid diluent through the inlet tube to the medicament containing chamber or cartridge. The adapter may be in the form of a tube or conduit in fluid communication with the inlet port and the housing chamber. The adapter may also be a conduit which connects a source of diluent and the housing chamber. The outlet port may also include, or be in fluid communication with, at least one outlet tube or channel, which is in fluid communication with the microdevice that will deliver the reconstituted fluid medicament to the subject. Microneedle(s), either hollow or solid, or a microabrader surface are the microdevices of preference so that the solution formed from the reconstituted medicament powder, can be administered intradermally or epidermally. The powder is reconstituted by a fluid diluent after rupture of the membranes on the opposed ends of the housing or cartridge, if present, creating a substantially instantaneous fluid stream through the cartridge, dissolving the powder particles into the fluid to form a solution. Fluidic pressure within the dry powder containing chamber, generated by the sizing of the at least one outlet port and the backpressure created by the insertion of the microdevice into the intradermal or epidermal site of the subject results in a device and method that essentially simultaneously reconstitutes the powdered material and delivers the reconstituted substance intradermally or epidermally.

In one aspect of the invention, the cartridge for use in the intradermal medicament delivery device and methods for its preparation and filling with medicament is described in U.S. application Ser. No. 09/879,517, filed Jun. 12, 2001, the contents of which are expressly incorporated herein by reference. In this embodiment, the cartridge includes a body having opposed ends, a passage through the body and through the opposed ends, a medicament is stored in the passage and burstable or rupturable or pierceable membranes cover and seal the passage at the opposed ends of the body. The burstable membranes can be ruptured either by pressure or by physically piercing the membrane with a piercing element, such as that shown in U.S. Pat. No. 6,443,152, issued on Sep. 3, 2002, the entire contents which are expressly incorporated herein by reference It may be of benefit to have the opposed ends of the cartridge body surrounding the passage be convex and the membranes are thereby stretched taut over the convex opposed ends and bonded thereto, sealing the passage. The opposed ends of the body may be frustoconical surrounding the passage and the membranes may comprise a thin burstable polyolefin film heat-sealed or fused to the opposed frustoconical ends of the body. An annular groove may be provided at the mid-portion of the cartridge body for ease of handling. Optionally, the interior passage may also contain baffles to deflect or disrupt the fluid flow there through.

The polyolefins include polyethylene, polypropylene, ethylene-alpha olefin copolymers. The polymeric films which form burstable membranes are preferentially oriented polyolefin films (membrane), preferably uniaxially oriented polyethylene films, angularly related, wherein the films oriented on the opposed ends of the cartridge are most preferably oriented at approximately right angles. Burstable membranes formed of preferentially or uniaxially oriented polyolefin film should be oriented at approximately right angles to the passage, which results in improved delivery of the medicament. Polyolefin films can be oriented by drawing in one or both mutually perpendicular directions in the plane of the film to impart strength thereto using methods known in the art.

Prototype testing indicates that the pressure-burstable membranes at the opposite ends of the cartridge in the delivery devices of this invention rupture nearly simultaneously using only a modest pressure. Where the membranes are preferentially or uniaxially oriented and perpendicular, the membranes each rupture in a slit near the center along the axis of the oriented films at approximately right angles to one another. Although not requisite for operation of the invention, it is theorized that this type of rupture requires the fluid to turn as the fluid is rapidly transmitted through the passage, mixing with and dissolving the medicament and entraining the fluid medicament through the slit formed in the second membrane. It has been found that when the fluid used to entrain the powdered medicament was in the form of a gas, the generally perpendicular orientation of the preferentially or uniaxially oriented films oriented at right angles in this embodiment resulted in an emitted dose of about 97%. Similar result would be expected with the fluid in the form of a liquid.

The employment of mechanical piercing elements enables the use of high barrier films, which may be too strong for bursting via use of pressure alone. Such high barrier films allow longer storage shelf life for the powder medicaments. Examples of high barrier films include, but are not limited to, higher gauge polyolefin monolayer and multilayer films, including those containing cyclo-olefins, metalized films, as well as other commercial films. FIG. 10 shows the water and oxygen barrier properties for a range of commercially available barrier films. Barrier properties of the materials making up the primary drug container are the most significant factors affecting drug stability. Oxidation can lead to drug degradation and precipitation. In addition the transport of water vapor into or out of the package will affect the drug concentration. High water vapor barrier is particularly critical for drugs stored in dry form since introduction of water may greatly accelerate certain degradation pathways in these drugs. Use of other examples of such films will be obvious to those skilled in the art.

The method of delivering a medicament to a subject comprises providing a medicament delivery device comprising a housing that comprises a chamber therein, an inlet port communicating with the chamber, and an outlet port communicating with said chamber; a cartridge, if utilized is placed within the housing chamber and the cartridge comprises a passage, a fluid receiving opening and a fluid discharge opening, both openings communicating with the passage. A dry powdered medicament is also contained within the housing chamber and preferably within the cartridge. A microdelivery device sized to penetrate into the stratum corneum, intradermal space, or to disrupt the stratum corneum is also comprised by the device.

At least one burstable membrane is sealingly attached to at least one of the housing openings or cartridge ports to retain the powdered medicament within the chamber or cartridge. Lastly an adapter communicating with the housing inlet port and adapted to communicate with a source of a fluid diluent is included in the device. The method then includes selecting a site for administration and then compressing the manually compressible fluid delivery device to deliver fluid to the inlet of the cartridge, rupturing the burstable membrane, dissolving or the medicament in the fluid and delivering the medicament to the selected site. Other attendant steps may be involved depending on the microdevice selected. A microneedle requires penetration of the stratum corneum prior to or concurrently with the actuation step. The microabrader requires the stratum corneum to be abraded prior to, jointly with, or after the actuation step.

Many of the current liquid based therapies require the addition of excipients or preservatives to ensure the integrity of the activity through storage. These excipients and preservatives may cause skin irritation. Dry powders are generally more stable and maintain activity without the use of a preservative and thereby possibly avoid skin irritation. The devices of the invention maintain the drug formulation as a dry stable form until immediately prior to delivery, prolonging its overall stability and storage lifetime.

It has been shown that Spray Freeze Dried (SFD) powders lend themselves to more instantaneous reconstitution into solution due to the porous morphology of the particles. This provides a benefit over other powder samples that are prepared by milling, lyophilization or spray drying, where significant agitation or mixing must occur to get the dry powder into solution prior to delivery. The ease of reconstitution of SFD powders permits the integration of all of the steps into one injection.

Additional baffles and other mixing elements may be added to the fluid path of the device, either in the housing or the cartridge, increasing the contact time between the diluent and the dry powder, ensuring proper mixing and reconstitution prior to delivery. In place of a syringe, diluent containing bladders or other diluent containing devices may be utilized to transfer the diluent into the dry powder container. Ports or rupture membranes may also be located between the diluent-containing device and the dry powder container to prevent re-filling or reuse of the device if so desired. This prevention of the refilling or reuse of the device could also be accomplished, for example, through the use of one-way valves, pressure fittings, or other such means.

The SFD powders may also allow the formation of supersaturated solutions. The rapid reconstitution and administration to the patient enabled by the devices of this invention permits solutions to be delivered to the patient without precipitation. This allows for reduced intradermal injection volumes for administration of a given dose. Reduced injection volume in turn may reduce the edema and erythema formed at the injection site, and thus reduce physiological perception of discomfort.

An additional benefit is that the use of dry powder forms of medicaments in a pre-filled, unit dose delivery device can eliminate the need for anti-microbial additives or other preservatives such as phenol or meta-cresol, which are found in many solution formulations of pharmaceuticals. Intradermal administration of phenolics and other preservatives is known to cause localized tissue damage, which is avoided by use of the in situ drug reconstitution method of delivery of this invention.

An additional benefit is the enhanced immune response that can be achieved with SFD vaccines administered with such a prefilled injection device such as this invention. Such SFD vaccines are described in co-pending U.S. patent application Ser. No. 10/299,012, filed on Nov. 19, 2002, the contents of which are expressly herein incorporated by reference.

The intradermal medicament delivery device, cartridge, and method of delivering a medicament to a recipient will now be described with reference to the accompanying drawings, in which preferred embodiments of the inventions are shown. However, as will be understood by those skilled in this art, the drawings are intended to be merely illustrative of preferred embodiments, and this invention should not be construed as limited to the embodiments disclosed in the drawings, wherein like numbers refer to like elements throughout.

One embodiment of the cartridge 20 for use with an intradermal medicament delivery device is shown in FIGS. 1 and 2. The cartridge 20 includes a body 22 having a passage 23 extending through the body 22 through the opposed ends 26 and 28. Also shown in FIG. 1 are optional baffles 49. The passage 23 is sealed at the opposed ends 26 and 28 of the body 22 by polymeric films or membranes preferably polyolefin films 30 and 32 respectively, having a burst pressure of less than 10 atmospheres, most preferably less than 5 atmospheres. The cartridge 20 fits within the chamber 29 defined by the two housing portions 42 and 45. Optional annular groove 51 in cartridge 20 is provided at the mid portion of the body 22 for ease of handling.

FIG. 6 shows the relation of cartridge 20 and an optional "O" ring 61, which helps properly position the cartridge 20 and provides a fluid tight seal when the cartridge 20 is secured in the chamber 29, formed by the housing portions 42 and 45. It is possible to achieve a fluid tight seal without the use of an "O" ring, in which case it would be omitted from the assembly. As shown in FIG. 6 the housing portion 42 containing the microneedle 50 contains a male threaded portion 43, which allows it to be releasably attached to the housing portion 45. Housing portion 45 preferably contains a Luer fitting 46 and having a female threaded portion 44 adapted to receive the threaded portion 43 of housing portion 42. The housing portions 42 and 45 fit together to form a fluid tight seal when all the components are secured within. This manner of joining also insures a tight fluid seal with reference to the "O" ring 61. The use of the threaded connectors 443 and 44 insures a more even pressure across the surface of the "O" ring. A second "O" ring 52 may also be employed, and would be placed at the opposite end of the cartridge 20 and the housing portion 45. (See FIG. 4).

FIG. 4 shows a second embodiment where housing portion 42 has been adapted for use with a micro abrader surface 62. The housing portion 42 has an optional recess 71 for receiving the "O" ring 61. The recess 71 positions the "O" ring 61 in place to hold the cartridge 20 in a desired position relative to an outlet 65 in fluid communication with tube or channel 64. Channel 64 is then in fluid communication with interior chamber 29, which contains cartridge 20. In use the contents of cartridge 20 will pass through outlet 65 to channel 64 and along passages 63 located on the sides of housing portion 42 so that the medicament is conveyed to the site of administration 62.

With regard to a releasable connection between the housing portions shown in the above preferred embodiments, it is also envisioned that means other than the pictured male and female threaded arrangement, such as a friction or a spring action clip involving a recess and a spring loaded protrusion or the like which cooperates with a recess to lock the halves in place.

FIGS. 5A-D show a schematic of an embodiment of a microneedle device in various stages of discharge. This embodiment incorporates piercing elements to mechanically rupture the membranes 30, 32. The depicted alternative version contains an integral housing 80 defining a chamber 79 into which the cartridge 20 is placed. The housing 80 contains a microneedle 50 integral with a protrusion 81, capable of mechanically rupturing the polymeric film 30, 32 placed at one end 26, 28 of the cartridge 20 and providing fluid communication with the cartridge passage 23 upon rupture of the polymeric film. A fluid-containing reservoir 82 contains a shaped protrusion 83, within reservoir chamber 85, which is capable of rupturing the polymeric film placed at one end 26, 28 of the cartridge and providing fluid communication with the cartridge passage 23 upon rupture of the polymeric film. The fluid containing reservoir 82 contains a seal 84 at the end opposite to the protrusion. The seal 84 is displaceable when pressure is applied to it, displacing the fluid contained within chamber 85 and through a passage in the protrusion 83 (not shown) and into the cartridge passage 23, dissolving the medicament contained therein to form a medicament solution. Alternatively, protrusion 83 is solid and a secondary passage is used to allow fluid communication. The medicament solution is then forced through the hollow microneedle 50. The fluid-containing reservoir 82 is movable within the chamber 79 of housing 80. Together, 80 and 82 form a liquid seal with the sides of the chamber 29. The movement of the fluid reservoir 82 causes the polymeric films to be mechanically ruptured by the integral microneedle protrusion 29 and the protrusion 83. The rupture of the polymeric films can be simultaneous or not. It is also possible to select films that do not require mechanical but rather can be ruptured by fluid pressure alone and modify the device appropriately to contain a microneedle without one or both of the integral protrusion 29 and the protrusion 83, depending on the placement of the polymeric film at the cartridge end 26, 28. The protrusion and the integral microneedle protrusion are coaxially aligned in this embodiment.

As will be understood from the above descriptions of the aspects of the invention and the following examples, the method of delivering a medicament to a recipient and the medicament delivery device of this invention preferably delivers the medicament at a relatively modest pressure to the recipient as compared to other devices requiring a lesser pressure, such as subcutaneous devices. In some embodiments of the medicament delivery device, fluid pressure is delivered to the inlet of the cartridge by a manually compressible fluid delivery device, such as a syringe or collapsible bulb, or bladder. In other embodiments of the invention, the fluid pressure is delivered via a pump. In the case of pressure burstable membranes, it is desired to have the burst pressure of the burstable membranes 30 and 32 between 1.2 and 10 atmospheres or more preferably less than 5 atmospheres and most preferably between 1.5 and 4 atmospheres, for ease of operation. These limited ranges do not apply for membranes that are mechanically burst. The passage 23 through the body of cartridge 20 serves as a vessel or reservoir containing a suitable medicament. As set forth above, and described further below, the medicament may be any medicament, drug or vaccine or combinations thereof used in the prevention, alleviation, treatment or cure of diseases. Examples of such medicaments are set forth below. In the disclosed embodiment, the passage 24 includes a unit dose of a powder medicament.

As shown in FIG. 1, the body 22 of the cartridge is preferably cylindrical having an intermediate or central V or U-shaped groove 51 for ease of handling and, where the cartridge is replaceable, the body portions on opposed sides of the central groove 51 may be symmetrical such that the cartridge 20 may be loaded into the intradermal medicament delivery device described below in either orientation, avoiding mistakes in assembly of the device. The passage 23 is preferably cylindrical, but may also be hourglass shaped, rectangular or shaped in other configuration depending upon the medicament, actuation means, or other considerations.

From the disclosure of Published U.S. Application 2003/0050602 published Mar. 13, 2003, herein incorporated by reference in its entirety, it is demonstrated that intradermal delivery produces higher backpressure than does subcutaneous delivery, and in some aspects of the invention the device utilizes that backpressure (from about 2.5 to about 20 psi) to assist in the substantially simultaneous reconstitution of the dried material in the device and the delivery of that reconstituted material to a subject. In the case of epidermal delivery, the backpressure is generated by the contact sealing of the device against the skin or alternatively by the sizing of such conduits that lead to the skin.

Figure 12:
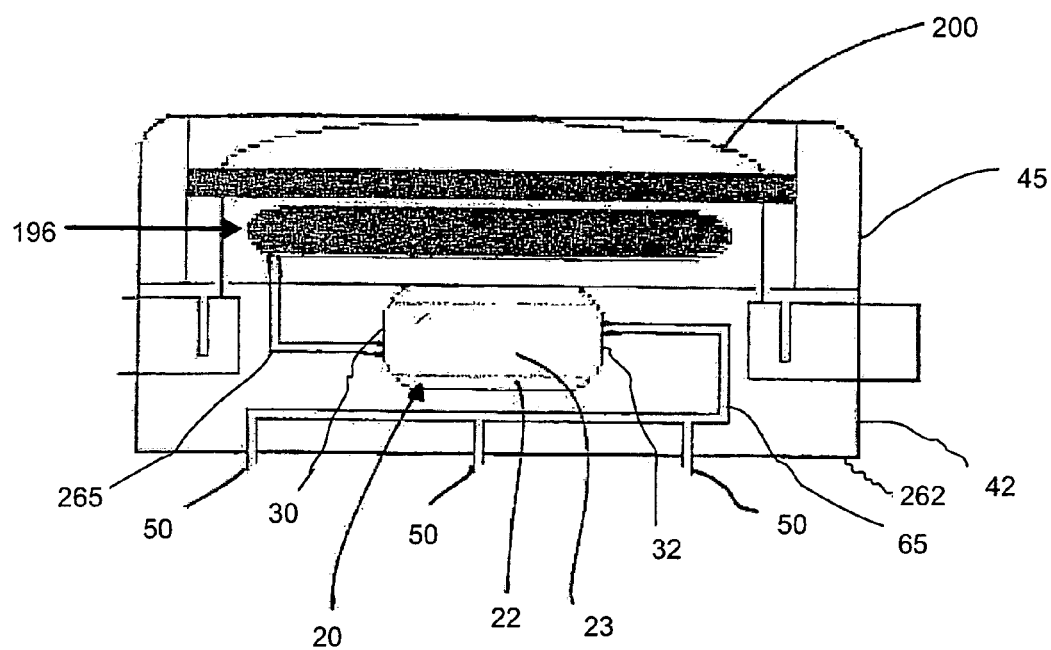

The device of FIG. 12 shows aspects of the invention incorporating automatic delivery of the reconstitution fluid via a pump. Housing 45 and 42 contain a reservoir 196 and driver 200. Reservoir 196 contains the reconstitution fluid which, when the device is activated, is expelled by driver 200 first to cartridge 20, then to a microdevice which is engaged to the patent. Driver 200 may be a Bellville spring, suitable pump or other drive mechanism known in the art. Sample drivers may be adapted from mechanisms described in U.S. patent application Ser. No. 10/112,757, filed Apr. 2, 2002 and U.S. Pat. Nos. 6,702,779 and 6,656,147 all of which describe such drive mechanisms in detail, and all of which are herein incorporated by reference in their entirety. When the driver is activated, fluid flows from reservoir 196 via first conduit 265, which flows past burstable membrane 30 on cartridge 20, through passage 23, past burstable membrane 32, through conduit 65 to microneedle(s) 50 and into the patient. The burstable membranes may be burst mechanically, as discussed previously, or by fluid pressure generated by driver 200.

Reservoir 196 in preferred embodiments is dimensioned to contain a reconstitution fluid to reconstitute a unit dose of a substance contained in cartridge 20 to be delivered to the patient. Preferably, membranes 30 and 32 and conduits 265 and 65 form a fluid-tight seal to cartridge 20, and membranes 30 and 32 are burst just prior to delivery of the fluid to the patent. Outer wall 262 supports one or more skin penetrating members 50, in this case microneedles. In some embodiments, microabraders are arranged in an array of rows and columns spaced apart by a substantially uniform distance. Typically, skin-penetrating members 50 are microneedles projecting from outer wall 262 at such a length to access the intradermal compartment and are arranged in an array designed to deliver an effective amount of a substance through the skin of a patient over a selected period of time. Typically, the needle array has an area of about 1 cm$^2$ to about 10 cm.$^2$, and preferably about 2-5 cm$^2$.

Figure 13:
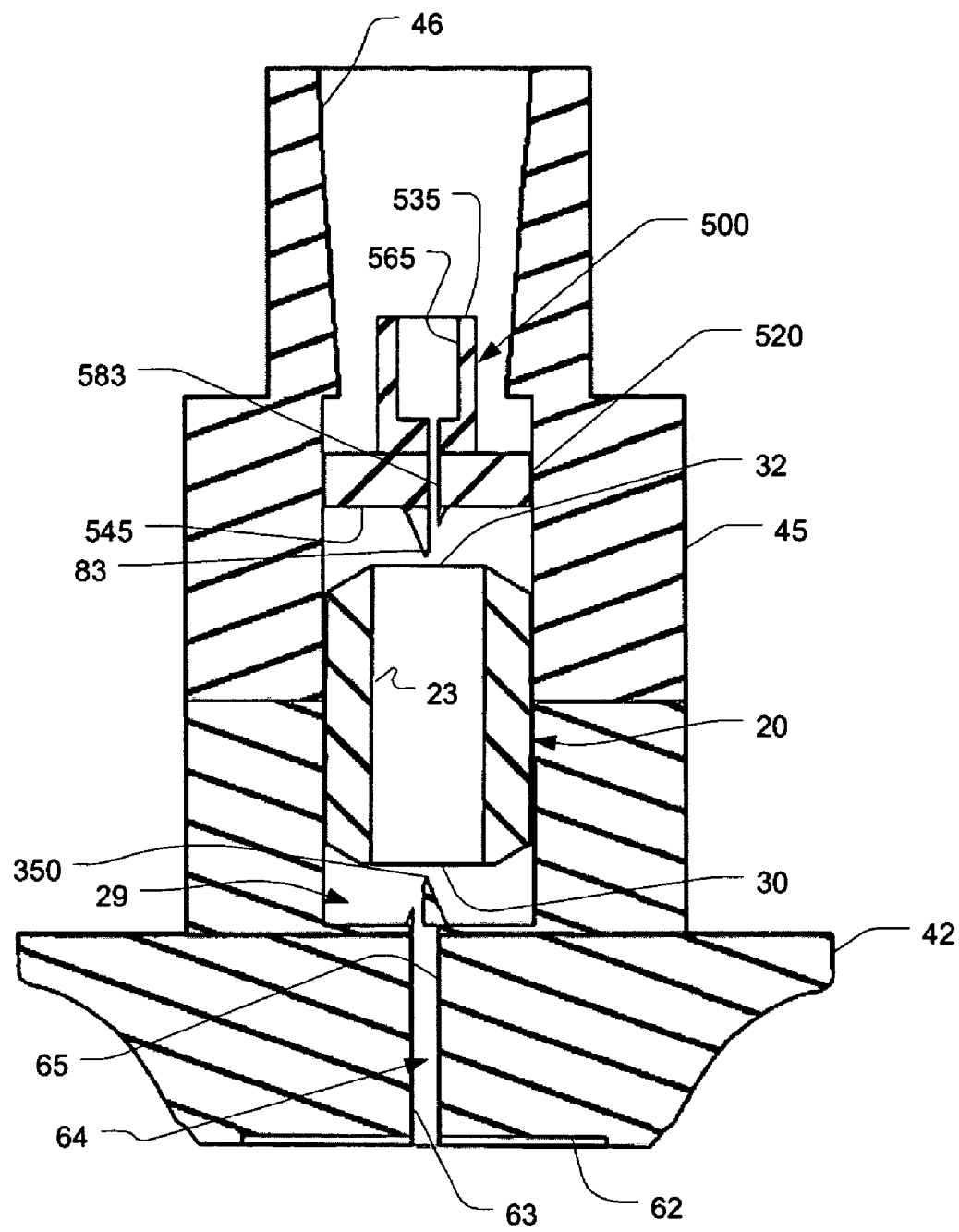

The device of FIG. 13 shows another aspect of the invention incorporating a sliding piercing element. In this embodiment, housing portion 42 has been adapted for use with a micro abrader surface 62. The housing portion 42 has been affixed to housing portion 45. Engagement of the two separate of housing portions 45, 42 is via a fluid-tight connection which may be accomplished via methods well known in the art, inter alia sonic welding. Alternatively, housing portions 45, 42 may be integrally formed from a single part. In some cases it may be desirable to have housing portions 45 and 42 permanently attached and in other cases a releasable attachment may be used. Interior chamber 29 is formed within housing portions 42 and 45. Chamber 29 contains cartridge 20 in a desired position relative to an outlet 65 in fluid communication with tube or channel 64. Cartridge 20 is slidably engaged to the walls of chamber 29 such that a substantial fluid-tight seal is maintained; yet cartridge 20 is free to move axially within chamber 29. Optionally, cartridge 20 is integrally formed into chamber 29 and is not movable. Optionally, at the distal end of chamber 29 is piercing element 350. Channel 64 is then in fluid communication with interior of chamber 29, which contains cartridge 20. In use, the contents of cartridge 20 will pass through outlet 65 to channel 64 and along passages 63, in this case, located at the central portion of housing portion 42 so that the medicament is conveyed to the site of administration 62. Alternatively, if a microneedle is used, the medicament is conveyed into the patient via a microneedle.

Chamber 29 also houses slidable carriage 500, which has distal end 545 and proximal end 535. On distal end 545 of carriage 500 is piercing element 83. Carriage 500 also has cavity 565 and passage 583 which are in fluid communication. An exterior portion 520 of carriage 500 engages the walls of chamber 29 such that carriage 500 is slidable along an axial direction. Additionally, the engagement of exterior portion 520 of carriage 500 to walls is substantially fluid-tight, such that fluid is preferentially routed through cavity 565 and subsequently through passage 583.

Housing portion 45 may contain a Luer fitting 46 or other fitting so that a fluid supply device, as described previously, may be attached to housing 45. As the device of FIG. 13 is affixed onto a fluid supply device or fluid line, proximal end 535 of carriage 500 interferes with the distal end of the fluid supply device or line, such that carriage 500 is moved axially in the distal direction, until such point that piercing element 83 pierces membrane 32. Alternatively, the axial movement of carriage 500 within chamber 29 is accomplished by the fluid pressure of the fluid supply impinging on the proximal half of carriage 500, within chamber 29, and no interference of carriage and distal end of the fluid supply is required. The device is then actuated such that fluid is expelled from the fluid supply through cavity 565 and passage 583 into cartridge 20 which houses the medicament, as described previously. Alternatively, in one particular embodiment, the fluid pressure builds within cartridge 20 such that cartridge 20 is moved distally within chamber 29 such that piercing element 350 pierces membrane 30. In another embodiment, cartridge 20 is moved distally by contact with the distal end 545 of carriage 500, such that, after membrane 32 is pierced, carriage 500 continues to move distally until piercing element 350 breaches membrane 30. In another embodiment where cartridge 20 is integrally formed or attached to the walls of chamber 29, bursting of membrane 30 is accomplished by pressure only.

As will be understood, the medicament delivery device and cartridge of this invention may be utilized to deliver various substances including medicaments via a intradermal or epidermal route used in the prevention, diagnosis, alleviation, treatment or cure of diseases. In addition, certain aspects of the delivery device of the invention may be useful in other routes of administration, such as inter alia parenteral, subcutaneous, intramuscular or intravenous delivery. Medicaments which may be delivered by the medicament delivery devices and methods of the invention by the may take other forms, other than the specific SFD powder which is described above such as inter alia lyophilized powders, particles, solutions, and suspensions. Specifically, medicaments in the forms of particles, micro-particles, nano-particles, which are entrained to form a suspension, may also be delivered by the devices and methods of the invention. A non-inclusive list of applicable substances may include, for example, (i) drugs such as Anti-Angiogenesis agents, Antisense, anti-ulcer, butorphanol, Calcitonin and analogs, COX-II inhibitors, desmopressin and analogs, dihydroergotamine, Dopamine agonists and antagonists, Enkephalins and other opioid peptides, Growth hormone and analogs (including growth hormone releasing hormone), Growth hormone antagonists, IgE suppressors, Insulin, insulinotropin and analogs, Ketamine, Kytril, Leutenizing hormone releasing hormone and analogs, lidocaine, metoclopramide, Midazolam, Narcotic analgesics, neuraminidase inhibitors, nicotine, Non-steroid anti-inflammatory agents, Oligosaccharides, ondansetron, Parathyroid hormone and analogs, Parathyroid hormone antagonists, Prostaglandin antagonists, Prostaglandins, Recombinant soluble receptors, scopolamine, Serotonin agonists and antagonists, Sildenafil, Terbutaline, vasopressin; (ii) vaccines with or without carriers/adjuvants such as prophylactics and therapeutic antigens (including but not limited to subunit protein, peptide and polysaccharide, polysaccharide conjugates, toxoids, genetic based vaccines, live attenuated, reassortant, inactivated, whole cells, viral and bacterial vectors) in connection with, arthritis, cholera, cocaine addiction, HIB, meningococcus, measles, mumps, rubella, varicella, yellow fever, Japanese encephalitis, dengue fever, Respiratory syncytial virus, *pneumococcus, streptococcus*, typhoid, influenza, hepatitis, including hepatitis A, B, C and E, polio, HIV, parainfluenza, *rotavirus*, CMV, chlamydia, non-typeable *haemophilus, moraxella catarrhalis*, human papilloma virus, tuberculosis including BCG, gonorrhoea, asthma, atherosclerosis, malaria, otitis media, *E-coli*, Alzheimer's, *H. Pylori, salmonella*, diabetes, cancer and herpes simplex; and (iii) other substances in all of the major therapeutics such as Agents for the common cold, Anti-addiction, anti-infectives, analgesics, anesthetics, anorexics, antiarthritics, anti-allergy agents, antiasthmatic agents, anticonvulsants, antidepressants, antidiabetic agents, anti-depressants, anti-diuretics, anti-emetics, antihistamines, anti-inflammatory agents, antimigraine preparations, antimotion sickness preparations, antinauseants, antineoplastics, anti-obesity, antiosteoporeteic, antiparkinsonism drugs, antipruritics, antipsychotics, antipyretics, antitussiers, anticholinergics, benzodiazepine antagonists, bone stimulating agents, bronchial dilators, central nervous system stimulants, corticosteroids, hormones, hypnotics, immunosuppressives, mucolytics, prostaglandins, proteins, peptides, polypeptides and other macromolecules, psychostimulants, rhinitis treatment, sedatives, sexual hypofunction, tranquilizers and vitamins including B12.

Example 1

Figure 7:
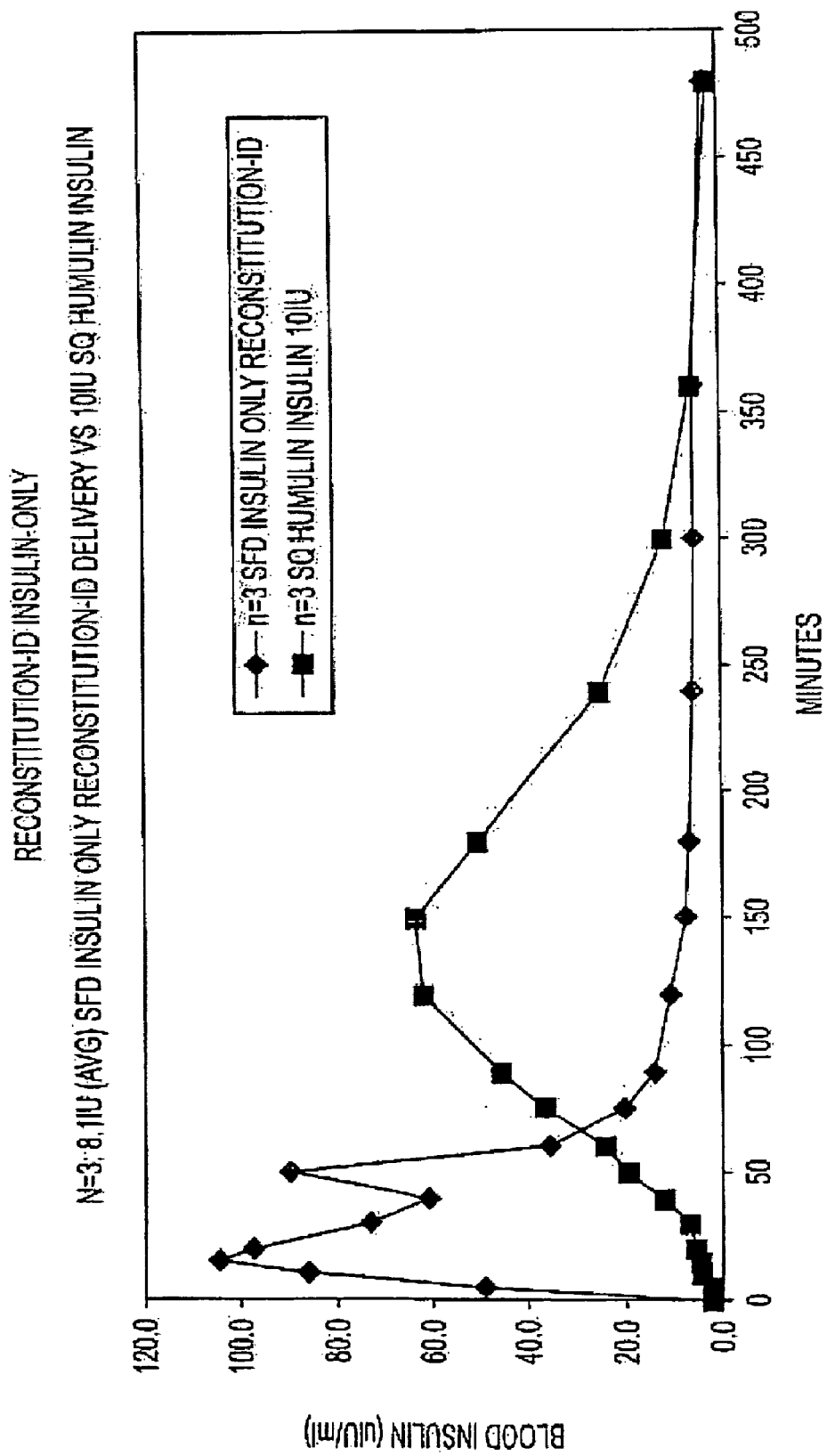
Figure 8:
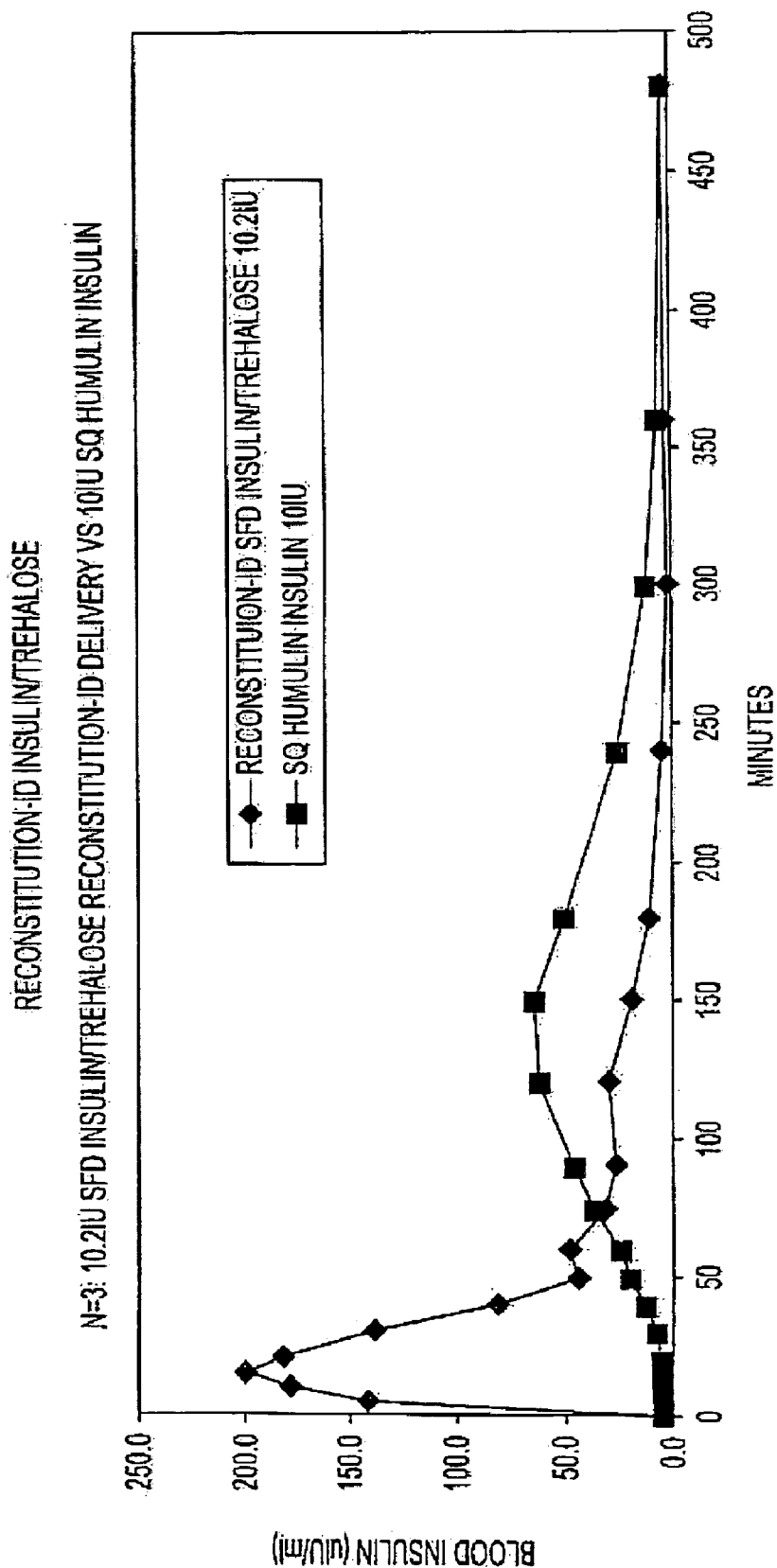

Spray-Freeze Dried (SFD) Insulin was prepared in the manner according to U.S. patent application Ser. Nos. 60/419,959 and 10/299,012, filed Oct. 22, 2002 and Nov. 19, 2002, respectively, the contents of which are herein expressly incorporated by reference. Single dosage amounts of a powder formulation of insulin were placed in the cartridge of devices in accord with that shown in FIG. 1, and sealed. The cartridge was then placed in the chamber of the device so that the ends aligned with the inlet and outlet. A 1.0 mm 34-gauge needle with an additional side port outlet was employed as the microdevice. A glass micro syringe was filled with diluent and positioned within the Luer fitting. The micro delivery device assembly was placed against the flank of a diabetic swine and the syringe plunger depressed, reconstituting the insulin powder, which was then injected into the animal. Blood samples were taken at 5, 10, 15, 20, 30, 40, 50, 60, 75, 90, 120, 150, 180, 240, 300, and 480 minutes. Blood glucose and insulin levels were recorded at each time point. The results are shown in FIG. 7 for SFD Insulin (8.1 IU) and for SQ Humulin Insulin (10 IU) and in FIG. 8 for SFD Insulin/trehalose (10.2 IU) and SQ Humulin (10 IU).

The results were analyzed. $C_{max}$ was found to be much higher for Reconstitution-ID delivery of SFD Insulin formulations than SQ Humulin injections. Reconstitution ID delivery allowed a more rapid onset of absorption versus SQ as measured by $t_{max}$ ($t_{max}$ Reconstitution=51 minutes vs. $t_{max}$ SQ=120 minutes).

The insulin formulations used during this trial were stored in a dessicator at room temperature for 4 months (Ins/Tre) and 10 months (Ins only). Both formulations retained their activity and readily went into solution at time of injection.

Example 2

Figure 9:
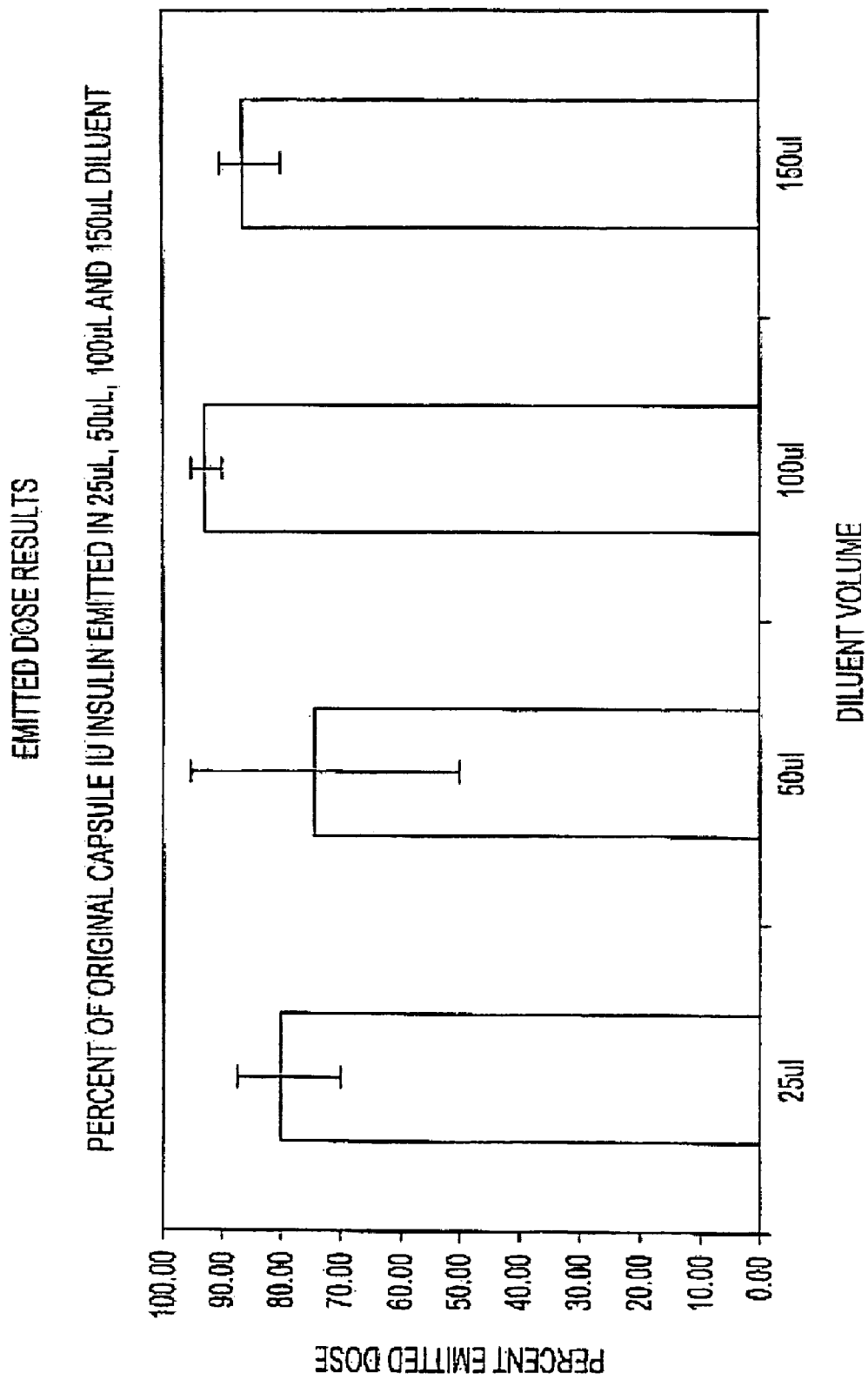

In order to quantify the level of emitted dose, medicament was injected into euthanized swine using devices in accordance to FIG. 1. The devices contained SFD Insulin/Trehalose at doses of 10.9 to 13.09 UI and were attached to diluent reservoirs containing either 25 μl, 50 μl, 100 μl, or 150 μl of diluent. The diluent used was 0.9% sodium chloride Injection USP. The devices were rinsed with 500 μl EDTA-solution after each injection. The rinses were analyzed using HPLC to determine non-emitted dose. The emitted dose was calculated by difference. Results are shown in FIG. 9. The emitted dose at 25 μl is 79.6%. The emitted dose at 100 μl is 92.6%. There is a loss of only 13% emitted dose with a 75% reduction in diluent volume. This reduction in emitted dose injection volume is beneficial to reduce the discomfort associated with injection.

The insulin formulations used were stored in a dessicator cabinet at room temperature for 4 months (Ins/Tre) and 10 months (Ins only).

Example 3

Figure 4:
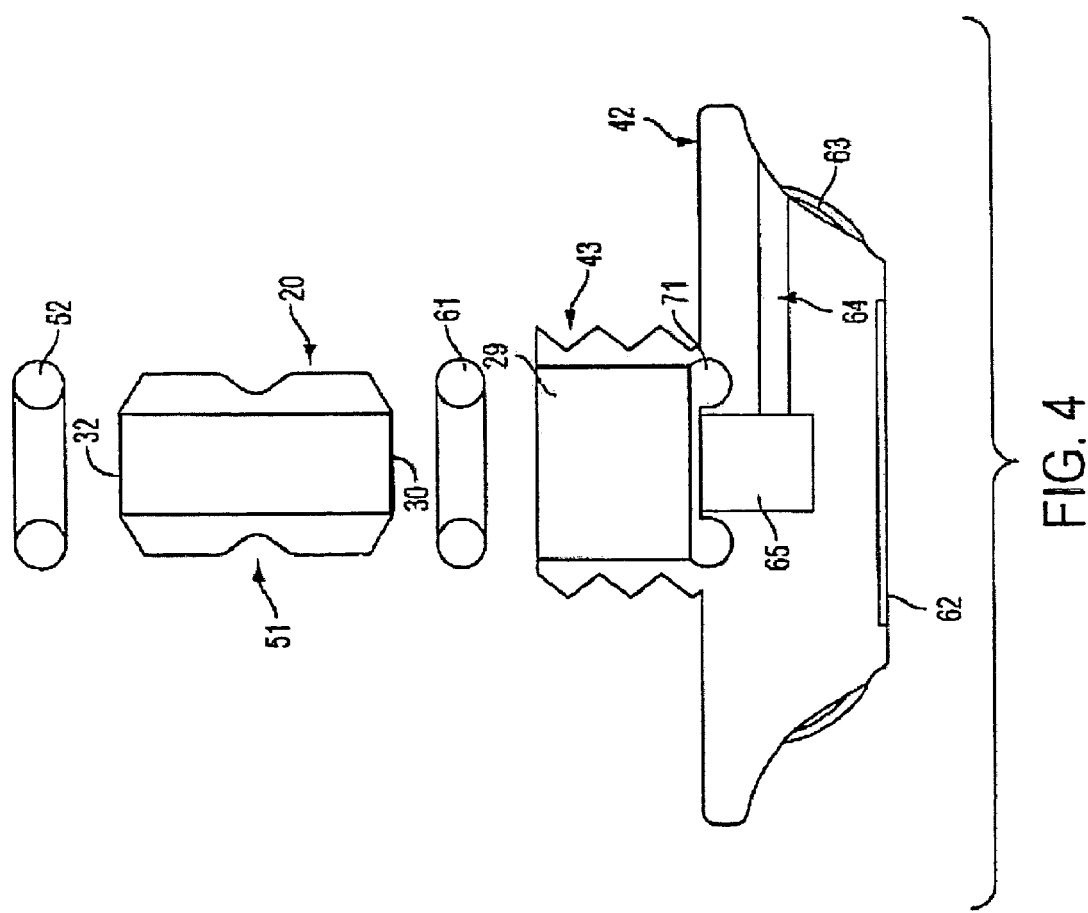
Figure 5A:
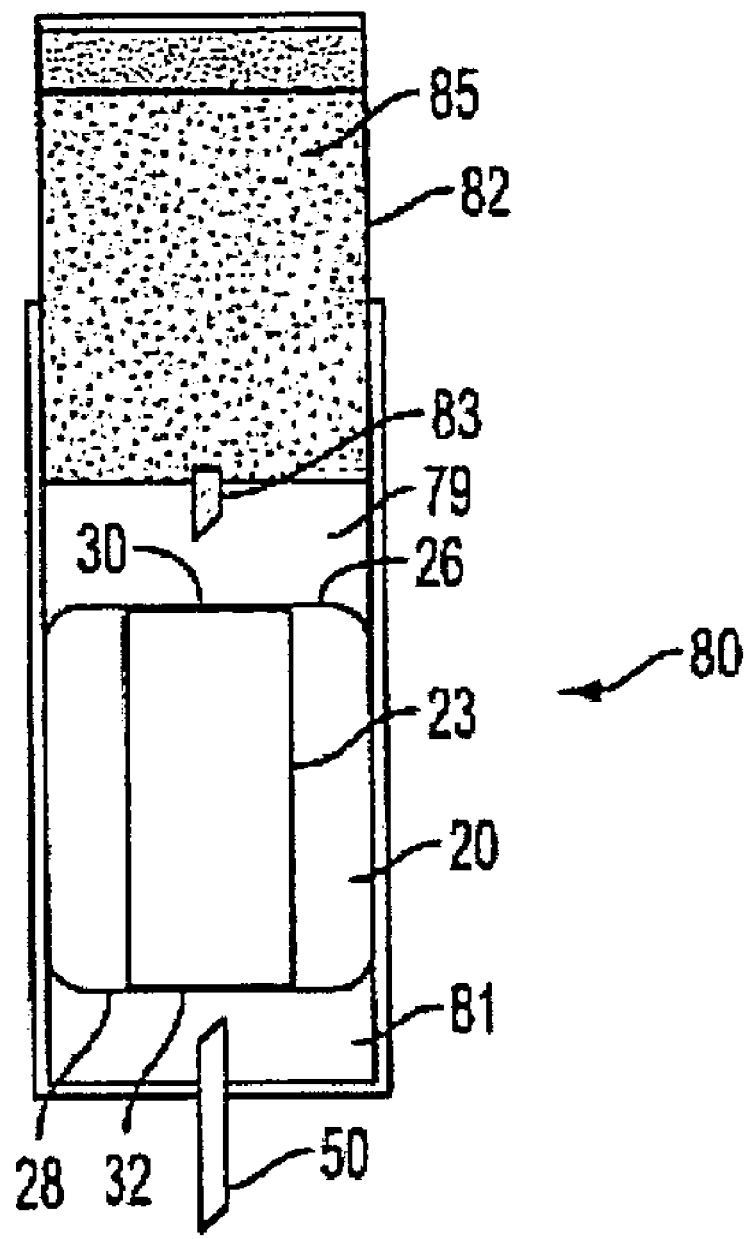
Figure 5B:
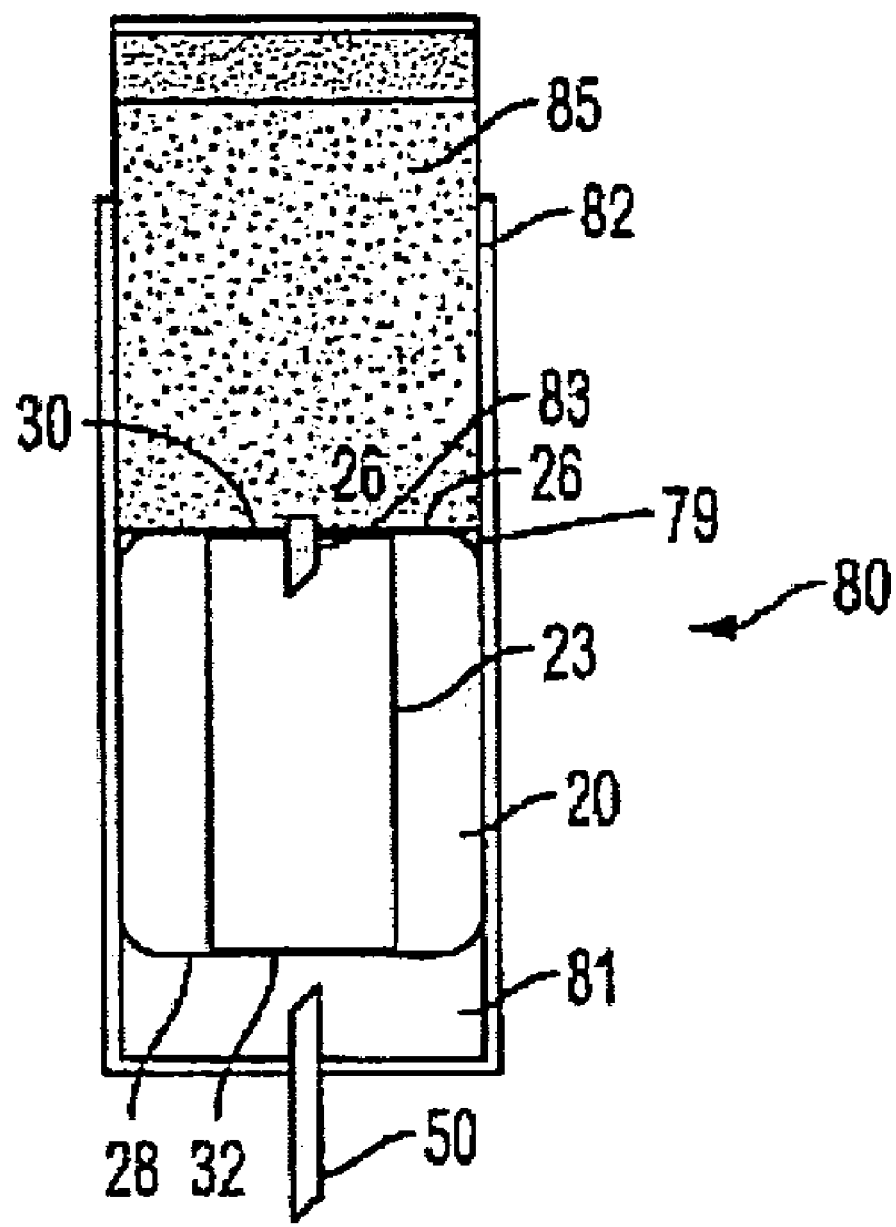
Figure 5C:
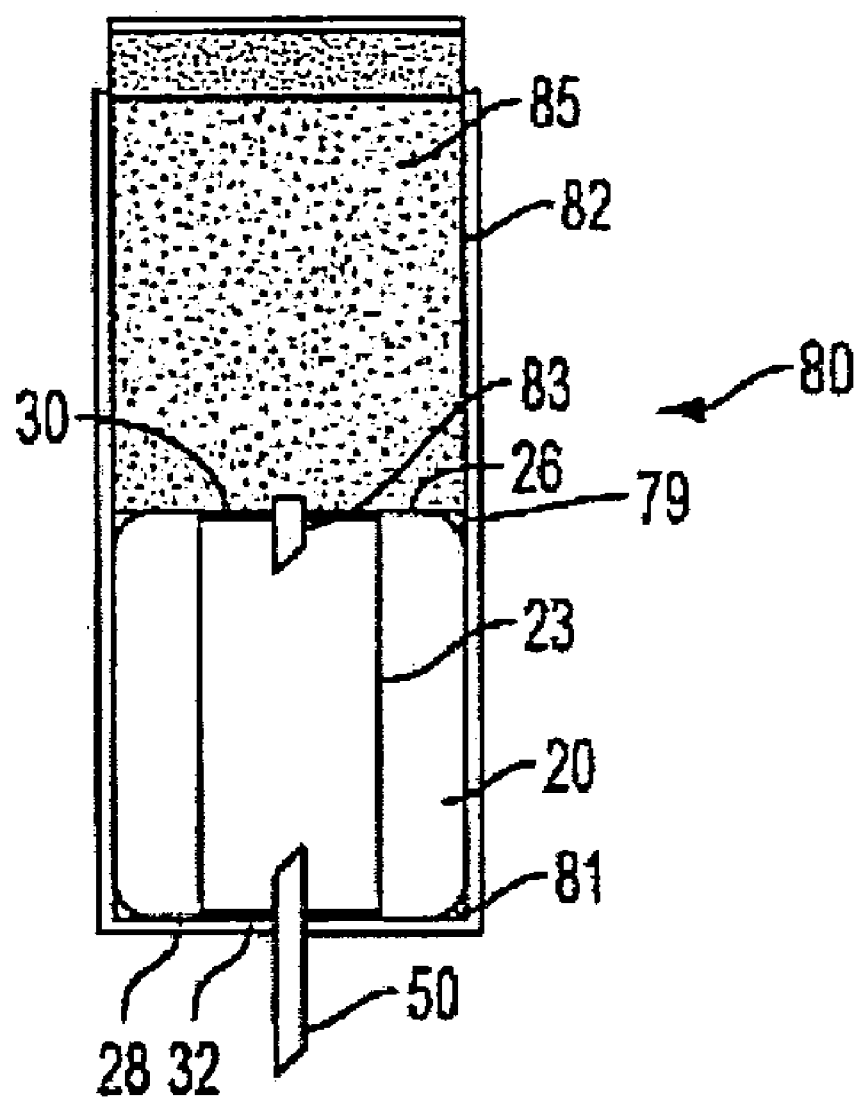
Figure 5D:
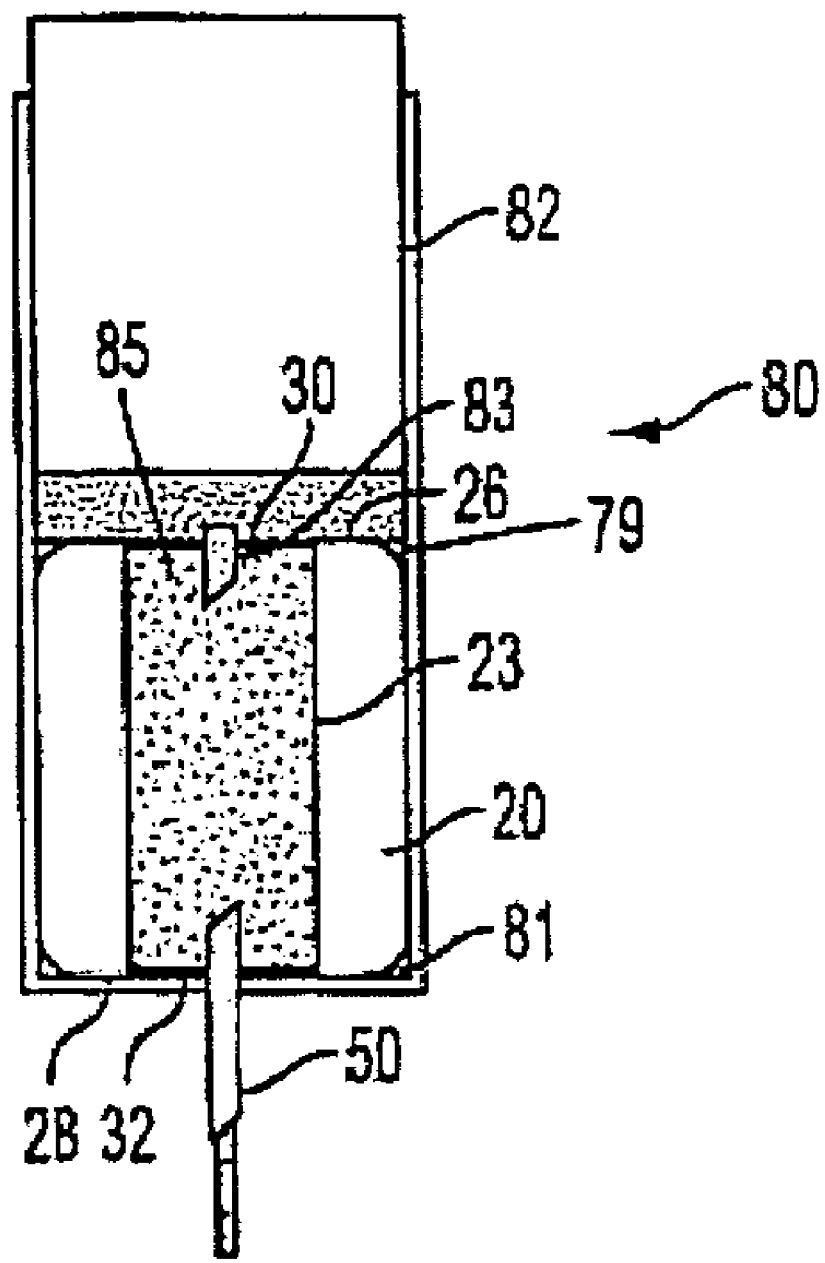
Figure 6:
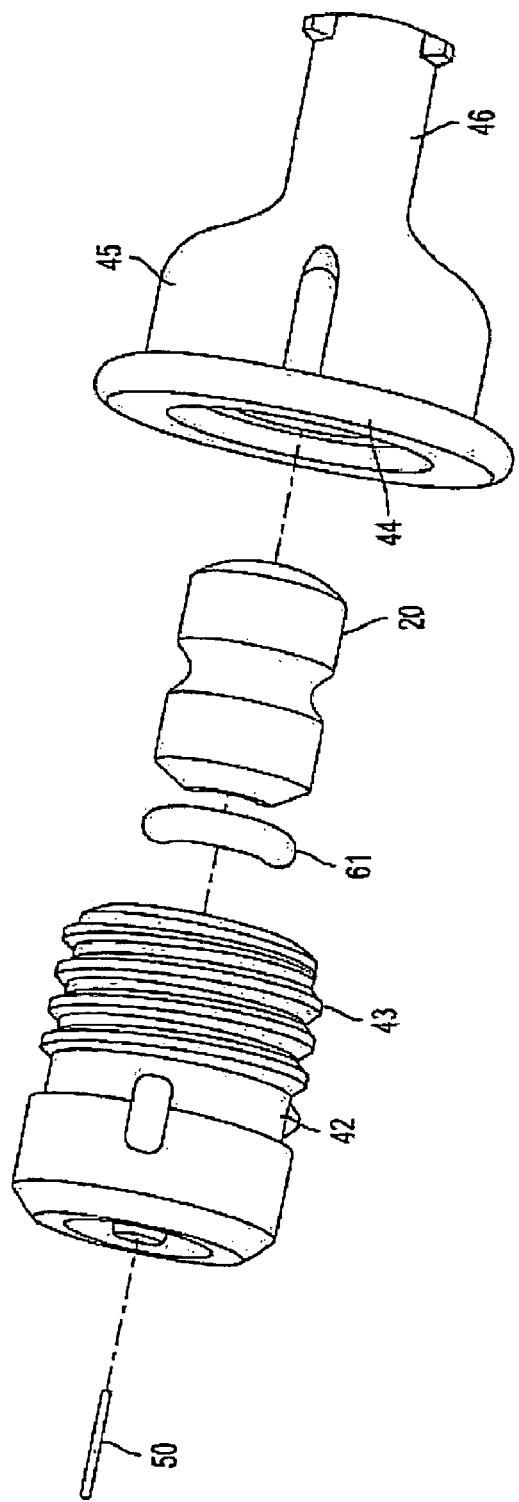
Figure 11:
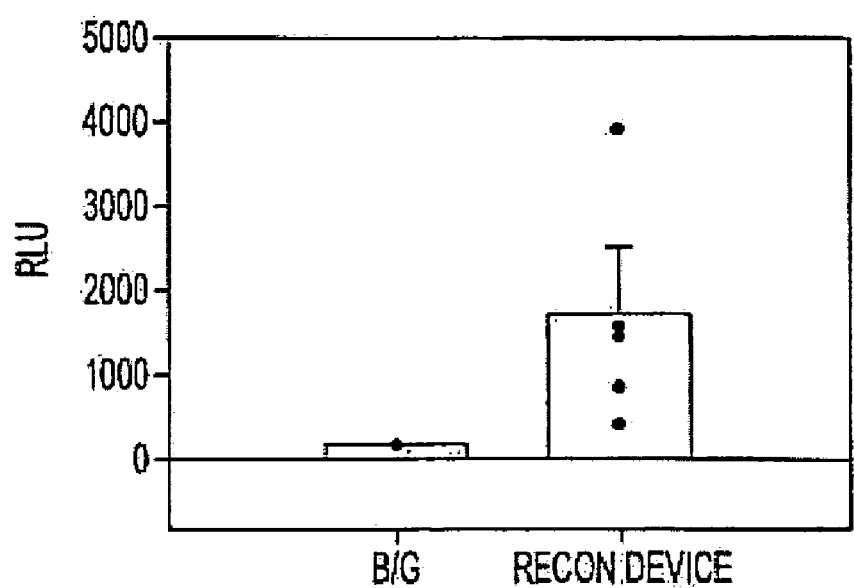

Luciferase plasmid (pCMV-Luc from Aldevron, 2 μg/mL in $H_2O$) was spray freeze-dried and loaded into cartridges by the process previously described. Each cartridge was loaded to contain 10 μg of plasmid. The loaded cartridge was inserted into a housing, which was in direct communication with a snap-fit adapted 1 cc tuberculin syringe. The housing itself was integrated with a microabrader device in accord with that shown in FIG. 4, with a fluid path terminating in a port opening just above the abrading surface, so that reconstituted medicament flowed onto the skin in front of the abrading surface during administration. The syringe was loaded with 250 μl of normal saline. After compensation for device deadspace, the amount of reconstituted SFD-plasmid delivered was approximately 50 μl. The syringe was slowly depressed, immediately reconstituting the SFD-plasmid and releasing a 50 μl drop of plasmid solution onto the shaved back of a Brown Norway Rat. The microabrader device was then passed over the plasmid solution 4 times in alternating up and down passes. This process was repeated on 4 other sites for 5 replicates of the condition. Treated sites were excised 24 hours post-treatment and analyzed for luminescence against untreated skin. The graph in FIG. 11 shows the results of this analysis. In FIG. 11 RLU=Relative luminescence units, B/G=Background (negative control), and the Reconstitution/Delivery Device was the microabrader device of FIG. 4.

Sites treated with the reconstituted Luciferase plasmid produced luminescence significantly above the negative control. Therefore, one may conclude that the cells in the rat skin were transfected with Luciferase plasmid and Luciferase protein was produced. Several conclusions can be drawn from this data. The SFD process did not disable the plasmid's ability to transfect cells. The passage of a fluid through the cartridge was sufficient to reconstitute the SFD-plasmid. The microabrader device successfully accessed living cells in the skin.

Thus, it is seen that an intra-dermal delivery device, having a membrane, a microdevice and a medicament and method of delivering medicament to the subject using the intradermal delivery device has been described and disclosed. It will be apparent that the present invention has been described herein with reference to certain preferred or exemplary embodiments. The preferred or exemplary embodiments described herein may be modified, changed, added to, or deviated from without departing from the intent, spirit and scope of the present invention.

The invention claimed is:

1. A dermal delivery device comprising:
a housing comprising a chamber, an inlet port communicating with said chamber, and an outlet port communicating with said chamber;
a cartridge, wherein said cartridge comprises a passage, a fluid receiving opening and a fluid discharge opening, both openings communicating with said passage; wherein said cartridge comprises opposed ends and said ends have convex surfaces and each end is sealed by a burstable membrane comprised of a polyolefin film having a thickness of between 0.3 and 1.5 mils stretched taut over each of said convex surfaces at said opposed ends of said cartridge and bonded to said convex surfaces, sealing said passage wherein said polyolefin film has a burst pressure of less than 5 atmospheres;
a dry powdered medicament retained by said burstable membranes within said cartridge;
a microdelivery device sized to penetrate into the intradermal space;
wherein at least one of said burstable membranes is sealingly attached to at least one of said ports; and
an adapter communicating with said inlet port and adapted to communicate with a source of a fluid diluent.

2. The dermal delivery device of claim 1, wherein said microdelivery device comprises one or more stratum corneum disrupting protrusions selected from the group consisting of microblades, and microneedles.

3. The dermal delivery device of claim 1, wherein said microdelivery device comprises one or more microneedles.

4. The dermal delivery device as defined in claim 3 wherein the one or more microneedles is a 1.0 mm length, 34 gauge needle.

5. The dermal delivery device of claim 1, further comprising a conduit in fluid communication with said outlet port and said microdelivery device.

6. The dermal delivery device of claim 1, further comprising a fluid diluent container permanently attached to said adapter.

7. The dermal delivery device of claim 1, wherein said adapter is a Luer connector for fluidly connecting said adapter to a syringe.

8. The dermal delivery device of claim 1, wherein said at least one burstable membrane is burstable by the application of pressure thereto.

9. The dermal delivery device of claim 1 wherein said adapter comprises an inlet tube communicating with said inlet port and said chamber having a Luer connector adapted to receive a syringe barrel.

10. The dermal delivery device as defined in claim 1, wherein said housing is formed of two releasably interconnected components and one of said components includes a generally cylindrical cartridge receiving chamber.

11. The dermal delivery device of claim 1, wherein said polyolefin film is a preferentially oriented polyolefin film and each of said oriented polyolefin films stretched over said opposed ends of said cartridge are oriented at different angles.

12. The dermal delivery device of claim 11, wherein said oriented polyolefin film is a uniaxially oriented polyethylene film, wherein said uniaxially oriented polyethylene film on one of said opposed ends of said cartridge is oriented at approximately right angles to the uniaxially oriented polyethylene film on the opposed end of said cartridge.

13. The dermal delivery device as defined in claim 1, wherein said thin burstable membranes have a burst pressure which is between 1.5 and 4 atmospheres.

14. The dermal delivery device of claim 1 wherein the housing is cylindrical and further comprises an opening for receiving the cartridge.

15. The dermal delivery device as defined in claim 1 wherein the medicament contains spray-freeze dried insulin.

16. The dermal delivery device as defined in claim 1 wherein the inlet and outlet ports are coaxially aligned.

17. The dermal delivery device as defined in claim 1 wherein the cartridge further comprises one or more baffles within the passage.

18. The dermal delivery device as defined in claim 1 further comprising an o-ring seal between at least one said burstable membrane and at least one of said ports.

19. A method for the intradermal delivery of a substance to a subject, said method comprising:
 positioning the device of claim 1 at a delivery site on the skin of a patient;
 intradermally administering the medicament by dispensing a diluent into the intradermal delivery device of claim 1 through the inlet port with sufficient force to rupture the at least one burstable membrane, thereby reconstituting the powdered medicament and delivering the reconstituted medicament through the outlet port to the microdevice to the intradermal region of the skin of the subject.

20. The method of claim 19, wherein the intradermal administration includes penetrating the stratum corneum of the skin with the microdevice prior to or concurrently with the delivery of the reconstituted medicament to the skin of the subject.

21. The method of claim 19, wherein the medicament contains spray-freeze dried insulin.

22. The method of claim 21, wherein the intradermal administration includes a higher peak concentration versus subcutaneous delivery as measured by $C_{max}$.

23. The method of claim 21, wherein the intradermal administration includes a more rapid onset of absorption versus subcutaneous delivery as measured by $t_{max}$.

* * * * *